United States Patent
Stephens

(10) Patent No.: US 9,988,360 B2
(45) Date of Patent: Jun. 5, 2018

(54) METHOD FOR PREPARATION OF 2-METHYL-1,2-BENZISOTHIAZOLIN-3-ONE

(71) Applicant: Rohm and Haas Company, Philadelphia, PA (US)

(72) Inventor: Randall W. Stephens, Perkasie, PA (US)

(73) Assignee: ROHM AND HAAS COMPANY, Philadelphia, PA (US)

( * ) Notice: Subject to any disclaimer, the term of this patent is extended or adjusted under 35 U.S.C. 154(b) by 0 days. days.

(21) Appl. No.: 15/526,003

(22) PCT Filed: Nov. 11, 2015

(86) PCT No.: PCT/US2015/060076
§ 371 (c)(1),
(2) Date: May 11, 2017

(87) PCT Pub. No.: WO2016/085655
PCT Pub. Date: Jun. 2, 2016

(65) Prior Publication Data
US 2017/0320840 A1    Nov. 9, 2017

Related U.S. Application Data

(60) Provisional application No. 62/084,720, filed on Nov. 26, 2014.

(51) Int. Cl.
*C07D 275/04* (2006.01)

(52) U.S. Cl.
CPC .................................. *C07D 275/04* (2013.01)

(58) Field of Classification Search
None
See application file for complete search history.

(56) References Cited

U.S. PATENT DOCUMENTS

| | | |
|---|---|---|
| 4,293,702 A | 10/1981 | Umemura et al. |
| 5,594,018 A | 1/1997 | Austin |
| 8,884,024 B1 | 11/2014 | Marsh |
| 9,139,540 B1 | 9/2015 | Emonds et al. |

FOREIGN PATENT DOCUMENTS

JP    1996277278    10/1996

OTHER PUBLICATIONS

Chem. Ber., (1928), vol. 61, pp. 1308-1316.
Zlotin, et aL., "Synthetic Utilization of Polynitroaromatic Compounds. 2. Synthesis of 4,6-Dinitro-1,2-benzisothlazol-3-ones and 4,6-Dinitro-1,2-benzisothiazoles from 2-Benzylthio-4,6-dinitrobenzamides," J. Org. Chem., vol. 65, p. 8439 (2000)).

*Primary Examiner* — Samantha L Shterengarts
(74) *Attorney, Agent, or Firm* — Kenneth Crimaldi

(57) ABSTRACT

A method for preparation of 2-methyl-1,2-benzisothiazolin-3-one from 1,2-benzisothiazolin-3-one by contacting 1,2-benzisothiazolin-3-one with an alkali metal hydroxide and dimethyl sulfate.

7 Claims, No Drawings

METHOD FOR PREPARATION OF 2-METHYL-1,2-BENZISOTHIAZOLIN-3-ONE

This invention relates to a method for preparation of 2-methyl-1,2-benzisothiazolin-3-one from 1,2-benzisothiazolin-3-one.

Methylation of 1,2-benzisothiazolin-3-one with agents such as methyl iodide and dimethyl sulfate is known. For example, A. Reissert & E. Manus, *Chem. Ber.*, (1928), vol. 61, pp. 1308-1316, disclose methylation of 1,2-benzisothiazolin-3-one with methyl iodide. However, this reaction produces mostly the O-alkylation product rather than 2-methyl-1,2-benzisothiazolin-3-one. There is a need for a more effective preparation of 2-methyl-1,2-benzisothiazolin-3-one from 1,2-benzisothiazolin-3-one.

The problem addressed by this invention is to provide an improved preparation of 2-methyl-1,2-benzisothiazolin-3-one from 1,2-benzisothiazolin-3-one.

STATEMENT OF THE INVENTION

The present invention is directed to a method for preparation of 2-methyl-1,2-benzisothiazolin-3-one from 1,2-benzisothiazolin-3-one; said method comprising contacting 1,2-benzisothiazolin-3-one with an alkali metal hydroxide and dimethyl sulfate.

DETAILED DESCRIPTION OF THE INVENTION

"BIT" is 1,2-benzisothiazolin-3-one. "MBIT" is 2-methyl-1,2-benzisothiazolin-3-one. Unless otherwise specified, temperatures are in degrees centigrade (° C.), references to percentages are percentages by weight (wt %) and amounts and ratios are on a weight basis. Unless otherwise specified, all operations were performed at room temperature (20-25° C.) and at atmospheric pressure (101 kPa).

Preferably, the peak temperature of the reaction mixture during dimethyl sulfate addition is no greater than 40° C., preferably no greater than 35° C., preferably no greater than 30° C., preferably no greater than 25° C., preferably no greater than 20° C., preferably no greater than 15° C., preferably no greater than 10° C.; preferably the peak temperature of the reaction mixture is at least −5° C., preferably at least 0° C., preferably at least 2° C., preferably at least 4° C.

Preferably, the alkali metal hydroxide is sodium, lithium or potassium hydroxide; preferably sodium or potassium hydroxide. Mixtures of alkali metal hydroxides may be used. Preferably, the ratio of moles of hydroxide to moles of BIT is at least 0.7/1, preferably at least 0.8/1, preferably at least 0.9/1, preferably at least 0.95/1, preferably at least 1/1; preferably no greater than 2/1, preferably no greater than 1.5/1, preferably no greater than 1.2/1, preferably no greater than 1.1/1, preferably no greater than 1.05/1.

Preferably, the reaction is carried out in a solvent or mixture of solvents. Preferred solvents include, e.g., water, acetonitrile and other polar aprotic solvents (e.g., N,N-dimethylformamide), and ethers (e.g., polyethylene glycol ethers, glymes, dibutyl ether, crown ethers). Water is especially preferred.

Preferably, BIT and the alkali metal hydroxide are combined (preferably in solvent(s)) and the resulting mixture is contacted with dimethyl sulfate. Preferably, BIT, solvent and the alkali metal hydroxide are combined to form a mixture comprising the alkali metal salt of BIT, and then dimethyl sulfate is added to the mixture comprising the alkali metal salt of BIT. Preferably, the dimethyl sulfate is added at a rate which allows the reaction temperature to remain within the preferred limits. This rate can be determined easily based on various factors including, e.g., cooling capacity of the equipment, size of the reactor, the temperature at the beginning of the addition, heat capacity of the reaction mixture and other factors known in the art.

The reaction time may be determined by the usual known methods, e.g., taking samples for analysis to determine completeness of alkylation, and will of course depend on the temperature and the exact nature of the reactants. In general, it is preferred that the reaction time is at least 10 minutes, preferably at least 15 minutes, preferably at least 30 minutes. The upper bound on the reaction time is not critical because the product is stable in the reaction mixture, but for practical reasons it is preferred that it not exceed 24 hours, preferably 12 hours, preferably 6 hours. The reaction time is measured starting at completion of dimethyl sulfate addition. Preferably, the reaction occurs at approximately normal atmospheric pressure (101 kPa±10%).

MBIT is the desired product resulting from methylation on the nitrogen atom of BIT ("N-alkylation") by dimethyl sulfate. 2-methoxy-1,2-benzisothiazole (MOBIT) is the undesired byproduct resulting from methylation on the carbonyl oxygen atom of BIT ("O-alkylation"). Separation of the N-methyl product from the O-methyl product may be achieved using standard techniques for separation of organic compounds, e.g., crystallization, distillation and extraction.

EXAMPLES

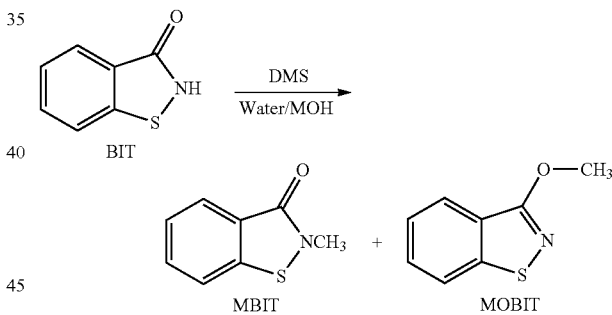

Example 1

To a 100 mL 3 neck round bottom flask equipped with a thermometer, external water bath, magnetic stirring bar and pressure equalizing addition funnel at room temperature was added 5.00 g of commercial grade 1,2-benzisothiazol-3 (2H)-one (85% BIT, 15% water; 0.0279 mol), 40 ml of water and 2.25 g of 50% sodium hydroxide solution (0.0281 mol). Stirring was initiated and over the course of approximately 5 minutes, 2.9 ml of dimethyl sulfate (DMS) was added using a gas tight syringe. The temperature remained within the range from 20-25° C. throughout the addition and subsequent reaction time. After a 30 minute reaction time, sodium hydroxide solution was added until the pH was above 9. To the stirred mixture was added 20 ml of ethyl acetate and the mixture was transferred to a separatory funnel using another 20 ml of solvent to rinse the residual contents of the flask into the separatory funnel. The layers were separated and the upper organic layer was washed with a small volume of saturated sodium chloride solution, separated, dried over anhydrous magnesium sulfate, and concentrated under vacuum to afford 4.23 g of light yellow oil in which a few crystals formed. Heating the sample allows induced the crystals to redissolve and this homogeneous sample was analyzed.

Analysis of this material by HPLC found it to contain 84% MBIT and 16% MOBIT, a calculated N-methylation ratio of 5.4 to 1.

Example 2

In a manner similar to Example 1 except that the sodium hydroxide was replaced with roughly an equal molar amount of potassium hydroxide was obtained 4.37 g of a crystal/oil mixture. The ratio of MBIT to MOBIT was calculated to be 5.4 to 1.

Example 3

In a manner similar to Example 2, except that the reaction temperature was lowered to and maintained at 5° C., was obtained 4.20 g of light yellow oil that crystallized over time. The ratio of MBIT to MOBIT was calculated to be 8.3 to 1.

Example 4

In a manner similar to Example 1 except that the sodium hydroxide was replaced with roughly an equal molar amount of lithium hydroxide was obtained 4.27 g of a crystal/oil mixture. The ratio of MBIT to MOBIT was calculated to be 5.6 to 1.

Example 5

In a manner similar to Example 1 except that 0.13 g of tetrabutylammonium bromide was added prior to the dimethyl sulfate addition was obtained 4.10 g of a waxy solid. The ratio of MBIT to MOBIT was calculated to be 5.6 to 1.

Comparative Example 1

To a 100 mL 3 neck round bottom flask equipped with a thermometer, magnetic stirring bar and pressure equalizing addition funnel was added 3.90 g potassium carbonate, 4.25 g of dried 1,2-benzisothiazol-3(2H)-one along with 50 mL of anhydrous acetonitrile. Stirring was initiated and the sand-like slurry became more flocculent over time. Over approximately 90 minutes, 2.9 mL of dimethyl sulfate was slowly added dropwise to the mixture. The reaction mixture thinned considerably over time and after holding for 30 minutes after the end of the dimethyl sulfate addition, 1 mL of water was added. The mixture was filtered and the liquid phase was concentrated to afford an oily residue. This material was partitioned between ethyl acetate and saturated sodium chloride solution to which a small amount of NaOH was added to destroy any remaining dimethyl sulfate. The layers were separated and upper organic layer was washed with a second volume of saturated sodium chloride solution (no added NaOH), separated, dried over anhydrous magnesium sulfate, and concentrated under vacuum to afford 4.87 g of a light tan oil.

Analysis of this material found it to contain 65.7% MBIT and 26.3% MOBIT, a calculated MBIT to MOBIT ratio of only 2.5:1.

The invention claimed is:

1. A method for preparation of 2-methyl-1,2-benzisothiazolin-3-one from 1,2-benzisothiazolin-3-one; said method comprising contacting 1,2-benzisothiazolin-3-one with sodium hydroxide, potassium hydroxide or a combination thereof and dimethyl sulfate; wherein 1,2-benzisothiazolin-3-one is contacted with sodium hydroxide, potassium hydroxide or a combination thereof to form a mixture and dimethyl sulfate is then added to the mixture.

2. The method of claim 1 in which the peak reaction temperature during dimethyl sulfate addition is from −5° C. to 40° C.

3. The method of claim 2 in which a ratio of moles of sodium hydroxide, potassium hydroxide or a combination thereof to moles of 1,2-benzisothiazolin-3-one is from 0.7/1 to 2/1.

4. The method of claim 3 in which the peak reaction temperature is no greater than 25° C.

5. The method of claim 4 in which the ratio of moles of sodium hydroxide, potassium hydroxide or a combination thereof to moles of 1,2-benzisothiazolin-3-one is from 0.9/1 to 1.2/1.

6. The method of claim 5 in which the peak reaction temperature is no greater than 10° C.

7. The method of claim 6 in which the solvent is water.

* * * * *